(12) United States Patent
Hacksteiner

(10) Patent No.: US 10,488,366 B2
(45) Date of Patent: Nov. 26, 2019

(54) APPARATUS AND METHOD FOR ELECTROCHEMICAL QUALITY CONTROL OF ELECTRICALLY CONDUCTING OBJECTS

(71) Applicant: MTI GmbH, Villach (AT)

(72) Inventor: Markus Hacksteiner, Villach (AT)

(73) Assignee: MTI GmbH, Villach (AT)

(*) Notice: Subject to any disclaimer, the term of this patent is extended or adjusted under 35 U.S.C. 154(b) by 105 days.

(21) Appl. No.: 15/522,244

(22) PCT Filed: Oct. 19, 2015

(86) PCT No.: PCT/AT2015/000133
§ 371 (c)(1),
(2) Date: Apr. 26, 2017

(87) PCT Pub. No.: WO2016/065379
PCT Pub. Date: May 6, 2016

(65) Prior Publication Data
US 2017/0350849 A1   Dec. 7, 2017

(30) Foreign Application Priority Data

Oct. 27, 2014 (AT) .................. A 786/2014

(51) Int. Cl.
*G01N 27/416* (2006.01)
*G01N 17/00* (2006.01)
(Continued)

(52) U.S. Cl.
CPC .......... *G01N 27/416* (2013.01); *G01N 17/00* (2013.01); *G01N 17/02* (2013.01); *H01L 22/14* (2013.01)

(58) Field of Classification Search
CPC ...... G01N 27/416; G01N 17/02; G01N 17/00; H01L 22/14
See application file for complete search history.

(56) References Cited

U.S. PATENT DOCUMENTS

| 4,575,678 A | 3/1986 | Hladky |
| 5,110,537 A | 5/1992 | Miura et al. |

(Continued)

FOREIGN PATENT DOCUMENTS

| DE | 37 15 881 A1 | 11/1988 |
| JP | H07-111286 A | 4/1995 |

OTHER PUBLICATIONS

Machine translation to English of DE 3715881 (Year: 1988).*
(Continued)

*Primary Examiner* — J. Christopher Ball
(74) *Attorney, Agent, or Firm* — Young & Thompson

(57) ABSTRACT

In order to test wafers, microchips and the like, electrical and/or electrochemical properties thereof are periodically measured using electrochemical processes and are stored. The test values are compared with each other in order to determine changes in the properties. The method is carried out using an apparatus designed as a measuring cell and including a test chamber which is located between an upper half-cell and a lower half-cell and through which electrolyte is conducted. The test chamber is closed by a cell cover which simultaneously presses a wafer against an O-seal in the direction of the upper half-cell. The opening forming the test chamber in the lower half-cell is closed by an O-seal, an anode disk and an anode cover.

22 Claims, 6 Drawing Sheets

Figure 1:
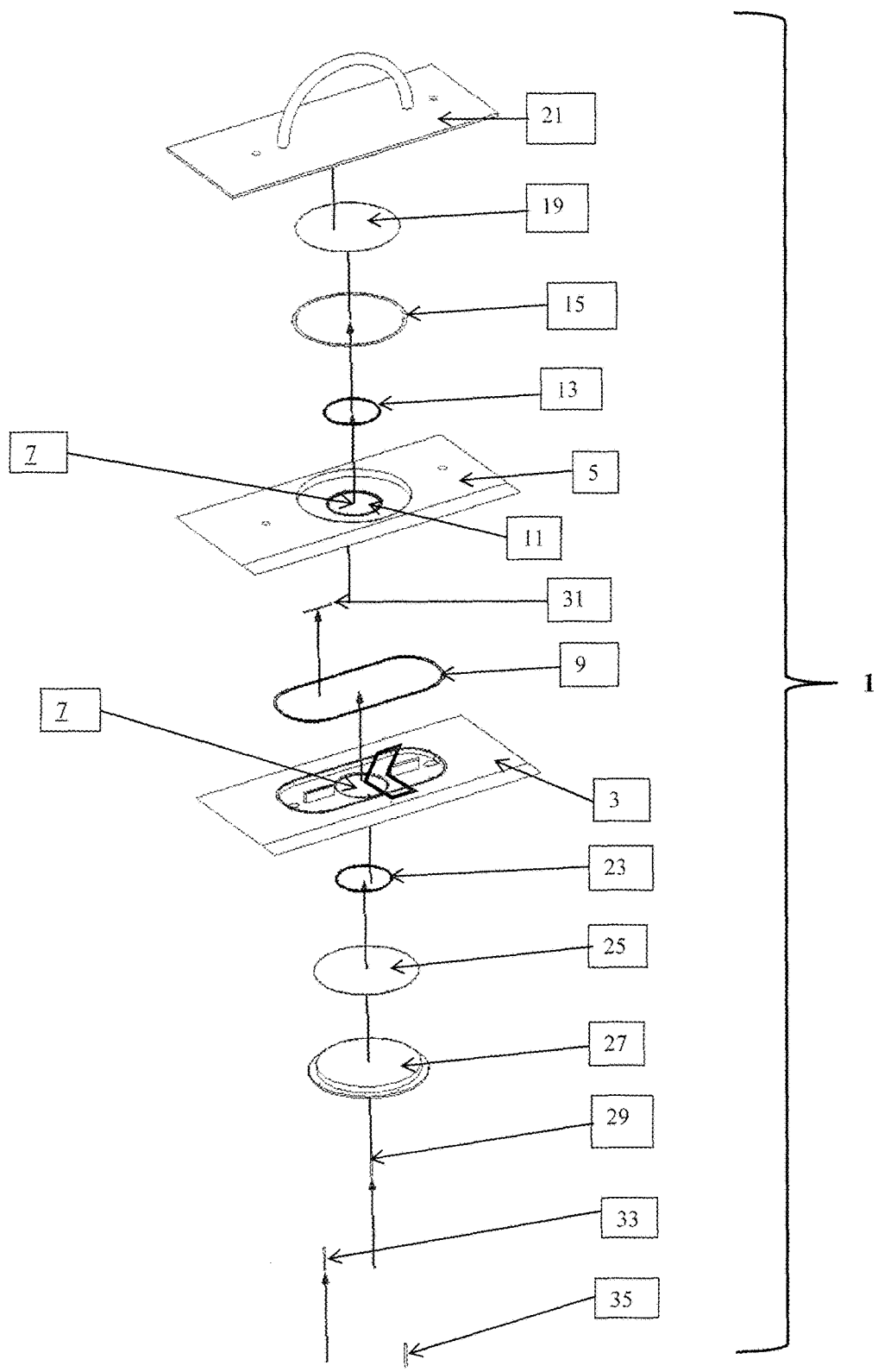

(51) Int. Cl.
   *G01N 17/02* (2006.01)
   *H01L 21/66* (2006.01)

(56) References Cited

U.S. PATENT DOCUMENTS

| | | |
|---|---|---|
| 5,820,746 A | 10/1998 | Kawaguchi et al. |
| 6,026,691 A | 2/2000 | Laird et al. |
| 2004/0016648 A1 | 1/2004 | Lubomirsky et al. |
| 2005/0109624 A1 | 5/2005 | King et al. |
| 2008/0223724 A1 | 9/2008 | Chen et al. |
| 2010/0200431 A1 | 8/2010 | Kim et al. |
| 2016/0363525 A1* | 12/2016 | Friedersdorf ............ G01N 3/02 |

OTHER PUBLICATIONS

Poelman et al., "Electrochemical study of different ageing tests for the evaluation of a cataphoretic epoxy primer on aluminium", Progress in Organic Coatings, vol. 54, No. 1, Sep. 2005.

Jaworski et al., "Copper ECD Process Control by Means of Electroanalysis Combined with Multi-way Data Decomposition Chemometric Techniques", ECS Transactions, vol. 6, Jan. 2008.

Baltzinger et al., "Contamination monitoring and analysis in semiconductor manufacturing", Semiconductor Technologies, pp. 57-78, Jan. 2010.

Pine Research Instrumentation, "Flat Cell for the Electrochemical Study of Corrosion and Coatings/Films", Apr. 2014 URL: https://www.pineinst.com/echem/files/docs/drp10055_flat_cell_product_guide.pdf Retrieved on Jan. 19, 2016.

International Search Report, dated Apr. 18, 2016, from corresponding PCT application.

AT Patent Office Search Report, dated Nov. 20, 2015, from corresponding AT application.

\* cited by examiner

APPARATUS AND METHOD FOR ELECTROCHEMICAL QUALITY CONTROL OF ELECTRICALLY CONDUCTING OBJECTS

The invention relates to a method with the characteristics of the introductory part of claim 1.

In addition, the invention relates to a device with the characteristics of the introductory part of claim 10.

From U.S. Pat. No. 5,820,746 A, it is known to bring a (semiconductor) wafer, which contains metal on its surface, into contact with ions, which corrode the metal, whereby constant-current electrolysis is applied in a galvanostat. The electrode potential of the metal is measured. In this way, on the one hand, the relationship between current value and time up until pitting occurs is to be determined, and on the other hand, a more critical current value is to be determined, based on which the metal is evaluated with respect to surface smoothness, corrosion resistance of the metal surface, resistance against pitting corrosion, segregation value, and concentration of trace elements in the metal, and grain size or grain dimensions in the metal.

A method for testing wafers is known from US 2010/0200431 A1. In this case, an electrolyte is applied to the metal-containing surface of the wafer. Using electrodes, which, on the one hand, are in contact with another area of the metal-containing surface not coated by electrolytes and, on the other hand, are in contact with the electrolyte-coated surface, the electrical resistance is measured. Thus, the amount of residues and the extent of corrosion in a side wall of the metal-containing surface of the wafer are to be determined.

JP H07111286 A deals with the evaluation of thin-film surfaces, whereby an electrolyte is applied and current is fed between a reference electrode, which is immersed in the electrolyte, and another electrode, which rests on the substrate. The resulting voltage between the drain and source areas embedded in the substrate is to be measured in order to detect contaminants.

A method and an apparatus for determining water quality are known from U.S. Pat. No. 5,110,537 A. In this case, changes in the quality of water are to be detected by the detection of changes in the rate of corrosion, whereby corrosion-caused changes in capacity between the electrodes are to be determined.

The object of the invention is to indicate a method and a device of the above-mentioned type, with which a continuous quality control of electrical products (electrically conducting objects), such as wafers, microchips, etc., and a process development are possible.

This object is achieved according to the invention with a method in which the characteristics of claim 1 are embodied.

Insofar as the device according to the invention is concerned, the object underlying the invention is achieved with a device that has the independent claim's characteristics that are directed toward the device.

Preferred and advantageous configurations of the method according to the invention, on the one hand, and the device according to the invention, on the other hand, are subjects of the dependent subclaims.

A major advantage of the method according to the invention relative to optical measuring methods (e.g., x-ray devices) lies in the fact that interaction reactions between, on the one hand, individual process results and, on the other hand, individual process media can be identified.

Interaction reaction: This can be oxidation, which is manifested by, e.g., the appearance of corrosion or leakage current. It can also be a reduction, which is manifested by, e.g., the formation of hydrogen. It can also be a chemical reaction.

Individual process result: e.g., metal layer or protective nitride layer; in general: electrically conductive layer or layer sandwich or conditioned/cleaned wafer surface.

Individual process medium: e.g., etching fluid or cleaning fluid; in general: electrically conductive fluid; this is used as a measuring fluid.

The term "electrical properties" is defined here as both electrical properties, such as resistance, capacity, etc., and as electrochemical properties (for example, corrosion by local element formation in the case of contaminated metal layers in the presence of a fluid/moisture or measuring fluid).

In the invention, electrical properties of objects are detected by, for example, the measurement of current-voltage curves, current-time curves, voltage-time curves (e.g., open circuit potential measurement), and impedance (general electrochemical methods), and characteristics of electrical properties, for example the curves, such as, for example, a rise in them at a certain point, which characterize the quality of a cathode surface (e.g., a wafer surface), a cathode layer or a cathode interface, are stored. As electrical properties, resistance and/or capacity can also be detected. Since this quality control, i.e., the measurement of current-voltage curves, current-time curves, voltage-time curves, impedance, etc., is performed periodically, e.g., once weekly, a change in the surface or layer quality can be detected (immediately) by a comparison of characteristics of electrical properties by statistical evaluation. It is thus possible to avoid losses in production since the production stability is monitored.

The method according to the invention and the device according to the invention can also be helpful within the scope of new individual process developments and individual process optimizations. Here, both the original electrolytes from the production processes and freely selectable electrolytes can be used. In addition to the high measuring sensitivity of the device and the method, in cases where original electrolytes are used, there is the additional advantage of not always needing the production facilities and thus blocking them for tests.

By the application of the method according to the invention and the use of the device according to the invention, it is also possible to perform early testing of interactions of a workpiece with an electrolyte with which it would only come into contact at a later time in production.

The device is therefore suitable in particular also for freeing up production facilities, by virtue of the fact that critical interactions can be checked in advance and immediately with subsequent method steps.

In particular in the case of freeing up production facilities, it is important that this assessment is quickly possible, since the production facilities for wafer manufacturing are very costly.

In one embodiment of the method according to the invention, it is possible to proceed in such a way that as electrical properties, current-voltage curves, current-time curves, voltage-time curves, and impedance, resistance, capacity, etc., can be detected.

In one embodiment of the method according to the invention, it is possible to proceed in such a way that as characteristics of the properties, the increase in current in the case of a defined voltage or the increase in voltage in the case of a defined time, various objects can be compared to one another.

In one embodiment of the method according to the invention, it is possible to proceed in such a way that electrical properties of objects are detected periodically and at specified intervals.

In one embodiment of the method according to the invention, it is possible to proceed in such a way that a comparison of characteristics of electrical properties of objects produced in succession is made.

In one embodiment of the method according to the invention, it is possible to proceed in such a way that a comparison of characteristics of electrical properties of objects produced in succession is made using statistical methods.

In one embodiment of the method according to the invention, it is possible to proceed in such a way that a comparison of characteristics of electrical properties of an object with the mean values of the characteristics of electrical properties of objects produced in advance is made.

In one embodiment of the method according to the invention, it is possible to proceed in such a way that the properties of electrically conductive layers, surfaces and/or interfaces of objects are detected.

The cell cover of the device according to the invention can contain a plug that can move normally with respect to the back side of the wafer and that is adapted by gas pressure to the back side of the wafer. Thus, the front side of the wafer presses on the ring seal, and the test chamber is therefore sealed. This has the advantage that wafers of various thicknesses can be inserted, e.g., bonded and thus thicker wafers, and this also has the advantage that the pressing force can be varied (ring seals of various hardnesses).

In one embodiment of the device according to the invention, the latter can be distinguished in that the anode is designed as an anode plate.

In one embodiment of the device according to the invention, the latter can be distinguished in that instead of the anode plate, a plate with at least two chemically inert electrodes, which are poled as a cathode and a reference electrode, is used. In this case, the anode plate can be used instead of the object.

In one embodiment of the device according to the invention, the latter can be distinguished in that the measuring cells comprise two cover parts and a middle part that is arranged between the latter, and in that the test chamber is provided in the middle part.

In one embodiment of the device according to the invention, the latter can be distinguished in that the middle part is formed by an upper half cell and a lower half cell.

In one embodiment of the device according to the invention, the latter can be distinguished in that the anode plate is arranged between an anode cover and the middle part, in particular the lower half cell thereof.

In one embodiment of the device according to the invention, the latter can be distinguished in that a seal is provided on the side of the middle part that is near to the object to be tested.

In one embodiment of the device according to the invention, the latter can be distinguished in that the seal rests on the objects to be tested, preferably on the edge or within the surface of the object.

In one embodiment of the device according to the invention, the latter can be distinguished in that in the test chamber, an opening is provided to let electrolytes into the test chamber and in that another opening is provided for electrolytes to exit from the test chamber.

In one embodiment of the device according to the invention, the latter can be distinguished in that the openings are provided in the lower half cell.

In one embodiment of the device according to the invention, the latter can be distinguished in that the test chamber is formed by the recesses in the half cells and is closed by the cover part.

In one embodiment of the device according to the invention, the latter can be distinguished in that a cover part is a cell cover and the other cover part is an anode cover.

In one embodiment of the device according to the invention, the latter can be distinguished in that the test chamber is inclined horizontally at an acute angle, in particular at 45°.

For example, the method according to the invention can be applied as follows:

When depositing metal layers, a contamination of the layer can occur, by which the layer is more base (i.e., more susceptible to corrosion). The contamination, however, cannot be detected with the usual equipment previously used in production (film thickness gauge, microscope, film resistance gauge). When a contaminated metal layer comes into contact with a solution at a later time in production (for example, two days later), the more base layer can be corroded by the contamination, which leads to losses in production.

A slow (creeping) incipient and increasing contamination of metal layers can be detected in a timely manner by electrochemical signals, which can be detected with the method according to the invention.

The invention thus makes it possible to schedule measures (e.g., a renewal of the electrolyte) in a timely manner, even before the contamination is critical, and leads to losses in production.

Figure 2:
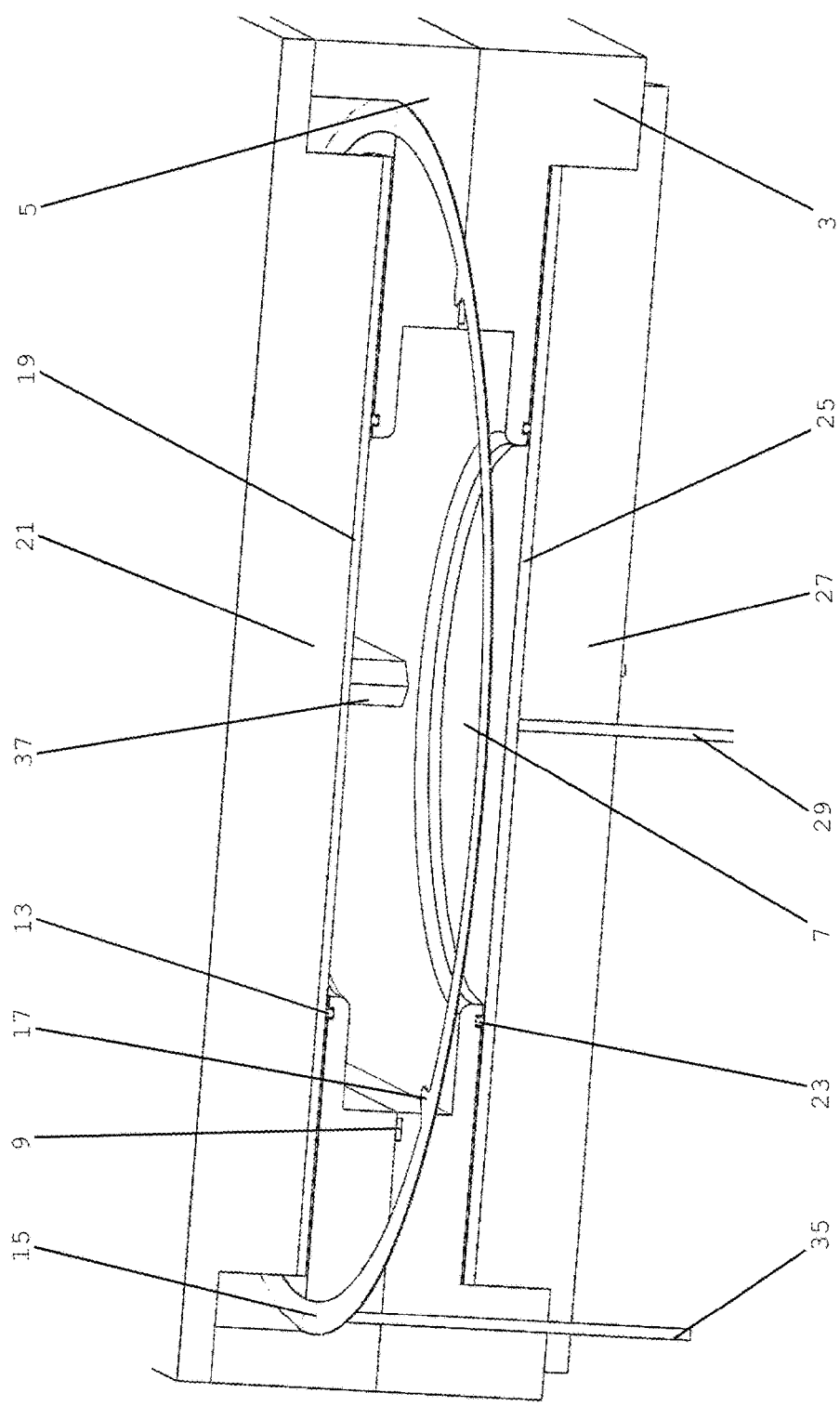
Figure 3:
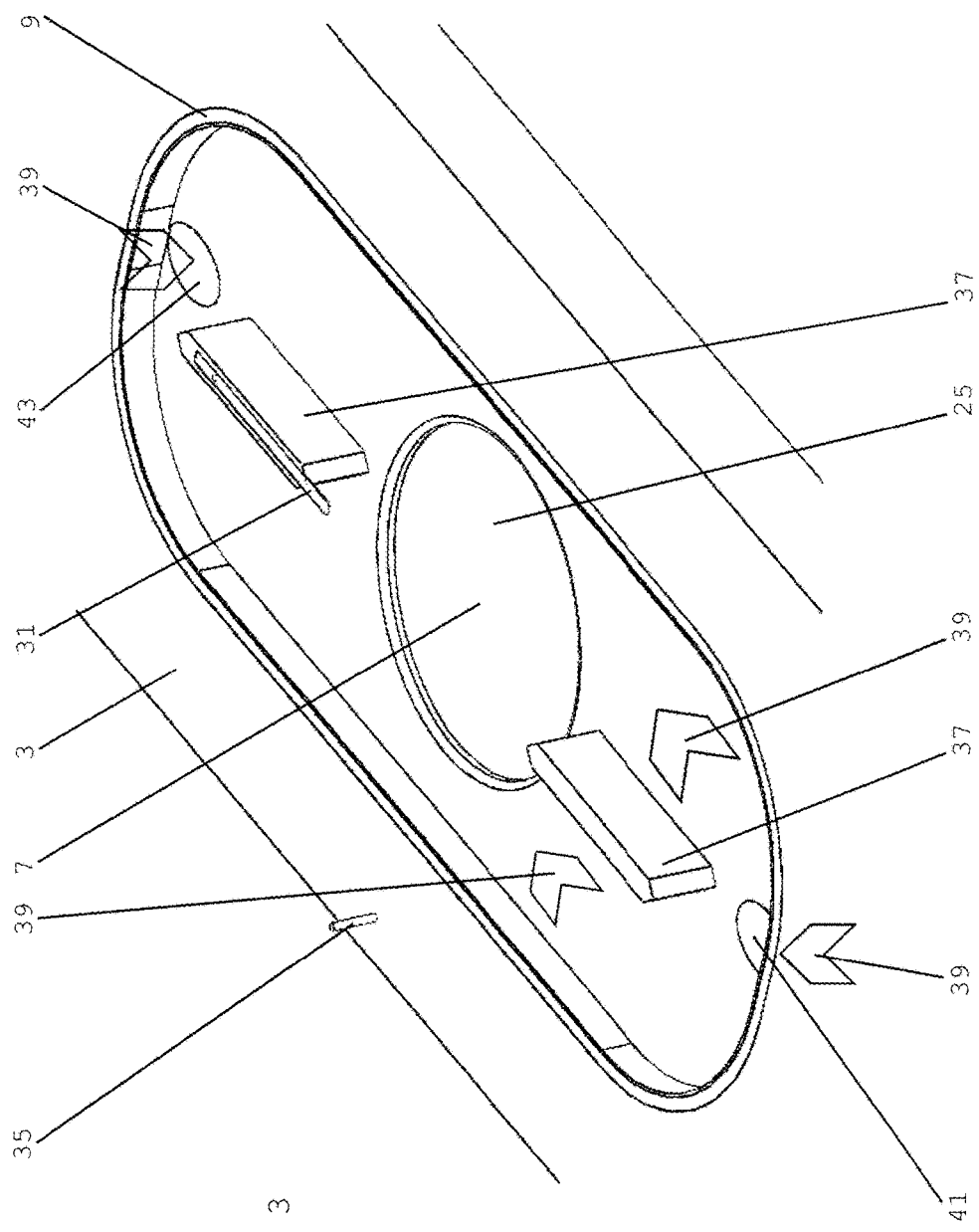
Figure 4:
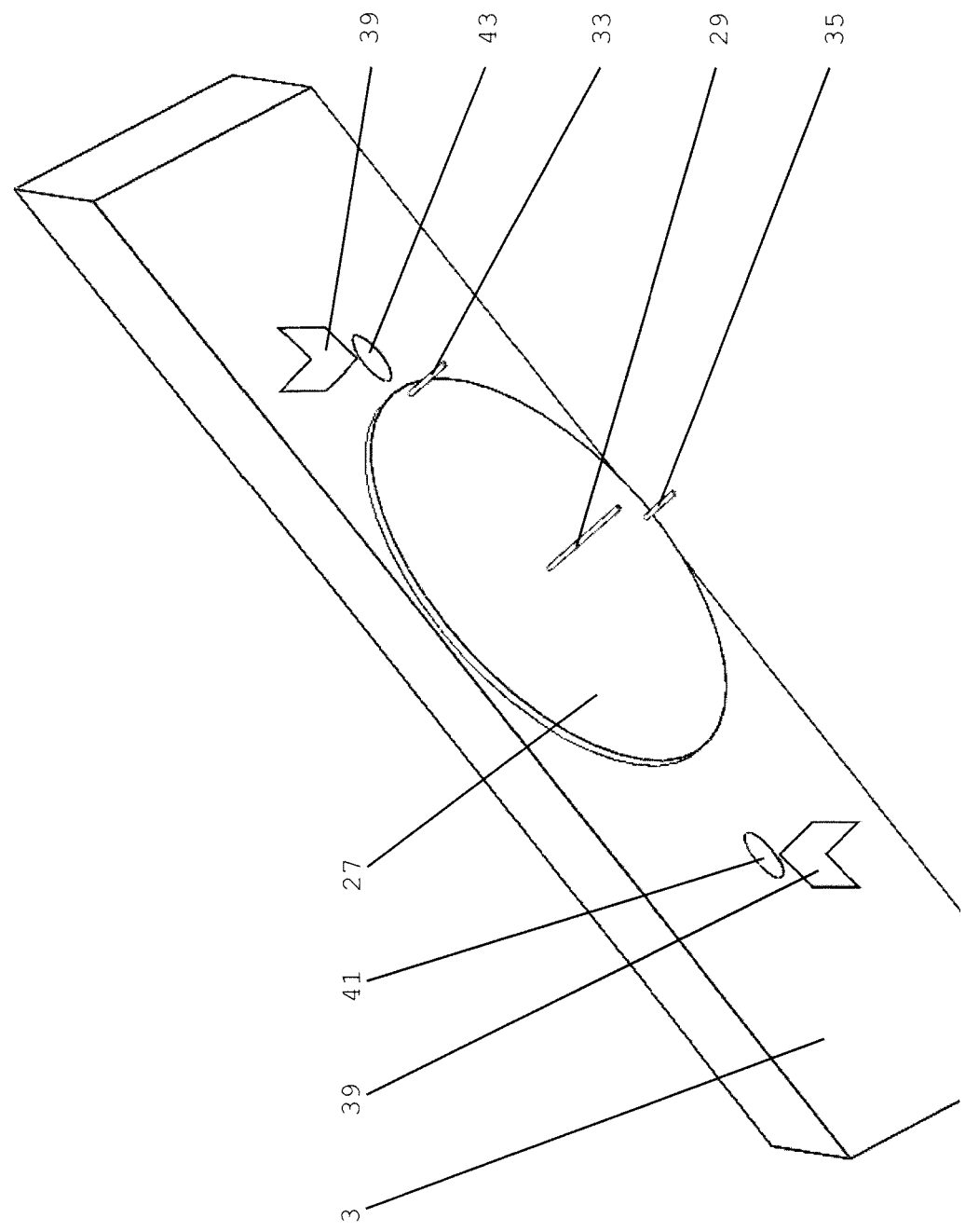
Figure 5:
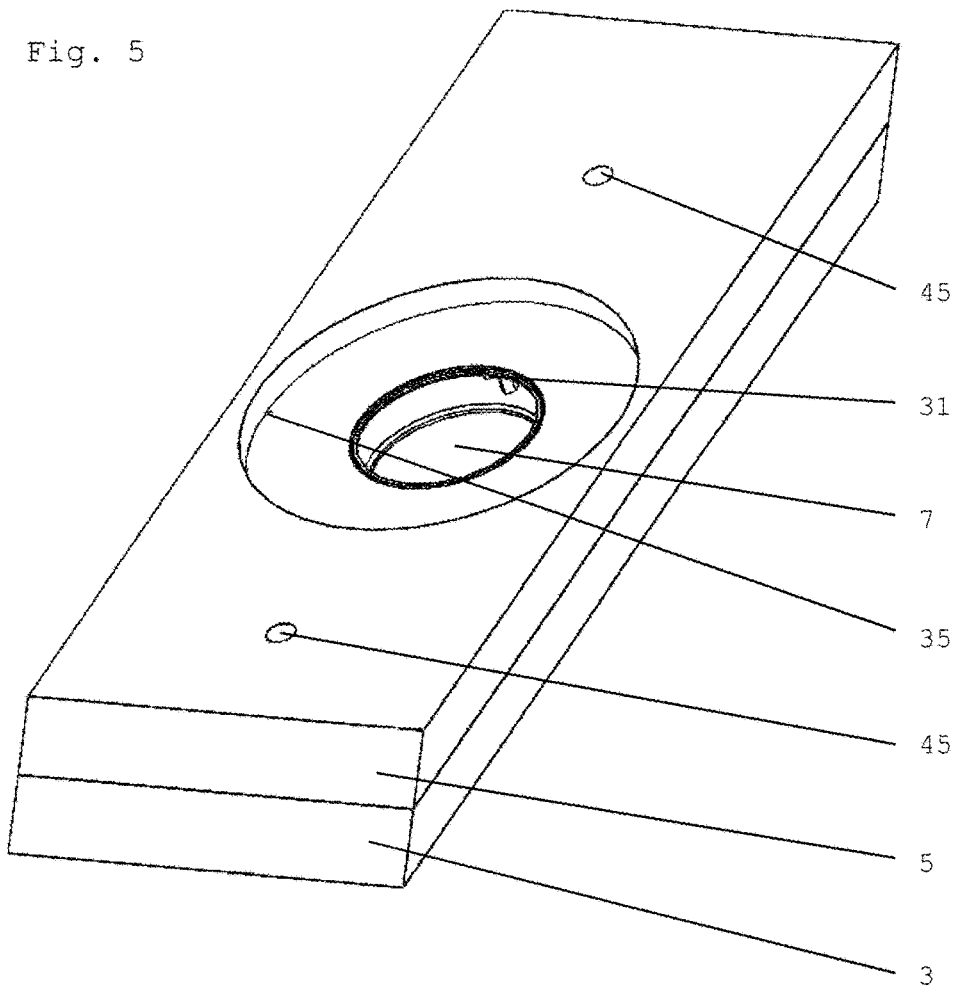
Figure 6:
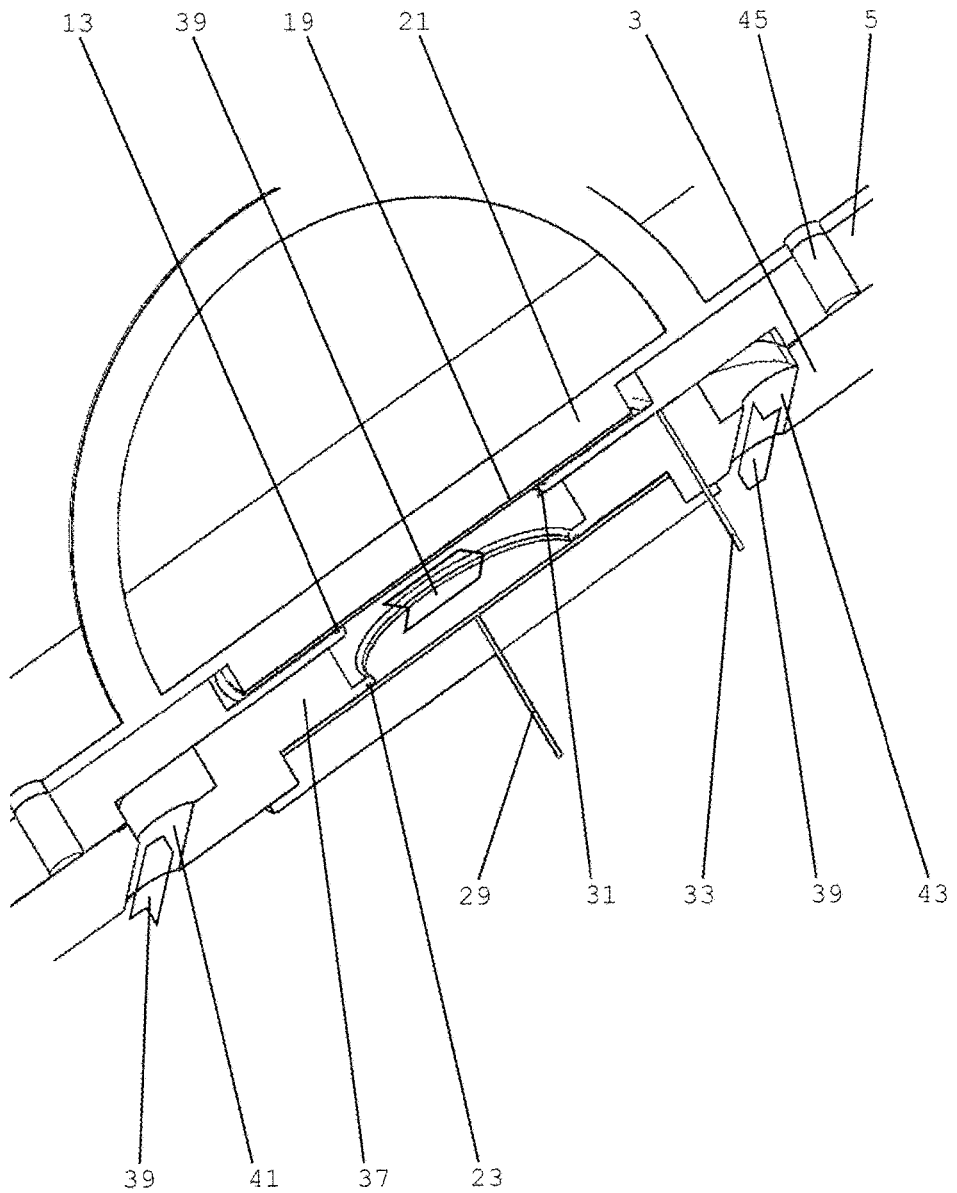

Additional details and characteristics of the method according to the invention and the device according to the invention follow from the description below with reference to the attached drawings. Here:

FIG. 1 shows a device according to the invention in an exploded depiction,

FIG. 2 shows a device according to the invention in section crosswise to the direction of flow, FIG. 3 shows a lower half cell, seen from above, in an oblique view, FIG. 4 shows the half cell from FIG. 3, seen from below, FIG. 5 shows a cell in a depiction seen from above, without a wafer, ring seal, contact film, and cell cover, and FIG. 6 shows a device according to the invention in section in the direction of flow.

In the embodiment shown in FIGS. 1 and 2, a device 1 that is designed as a measuring cell according to the invention comprises as essential components a lower half cell 3 and an upper half cell 5. Between the lower half cell 3 and the upper half cell 5, a flat seal 9 is arranged for sealing a test chamber 7, which is arranged between the half cells 3 and 5.

A ring seal 13 is provided encircling an opening 11 in the upper half cell 5. Outside of the ring seal 13, there is a film 15 with contact pins 17 for contacting the wafer 19. The wafer 19 to be tested is placed with its front side downward on the contact pins 17. Finally, the device 1 according to the invention is closed off above by a cell cover 21.

On the underside of the lower half cell 3, a ring seal 23 is provided, whereby the ring seal 23, for example in the form of an O-ring, is provided between the lower half cell 3 (underside thereof) and an anode plate 25. Below, i.e., outside of, the anode plate 25, an anode cover 27 is provided. In the area of the anode cover 27, an anode contact 29 is provided. Also, two or more contacts, e.g., on the edge of the anode plate 25, can also be provided.

In a recess in the lower half cell 3, a reference electrode 31 is arranged, which electrode is electrically contacted using a reference electrode contact 33. The wafer 19, which is oriented with its front side downward, i.e., in the direction toward the upper half cell 5, is contacted via a contact 35 and the film 15. The contact 35 is guided from below until it touches the film 15.

FIG. 2 shows the device 1 in the assembled state. FIG. 2 also shows that the test chamber 7 is formed by (round) recesses in the lower half cell 3 and in the upper half cell 5. In the test chamber 7, guides 37 are provided, which guides are used to direct the flow of electrolyte through the test chamber 7 and in addition improve the stiffness of the cell geometry.

FIG. 3 again shows how the reference electrode 31 is arranged on the top side of the lower half cell 3. The reference electrode 31 lies in a groovelike recess of one guide 37, which is arranged on the top side (side facing the upper half cell 5) of the lower half cell 3. Also, the contact 35 to the film 15 with the contact pins 17 is shown in FIG. 3.

In FIG. 3, the flow of the electrolyte through the test chamber 7 is symbolized by arrows 39. The electrolyte enters through an opening 41 into the test chamber 7 and leaves the latter again through an opening 43.

FIG. 4 shows the lower half cell 3, seen from below, and how the anode contact 29 is guided through the anode cover 27 until it is adjacent to the anode plate 25. In addition, FIG. 4 also shows the position of the reference electrode contact 33.

In addition, FIG. 4 shows the inlet opening 41 and the outlet opening 43 for the electrolyte, which is directed through the cavity (=test chamber 7), which is formed between the lower half cell 3 and the upper half cell 5.

FIG. 5 shows the upper half cell 5 and the lower half cell 3 as well as the components arranged in between, but without O-ring 13, wafer 19 and film 15 and without cell cover 21.

FIG. 6 shows a partial cross-sectional view (cross-sectional plane crosswise to the cross-sectional plane of FIG. 2, i.e., in the direction of flow from the electrolyte through the test chamber 7) of components of the device 1 according to the invention.

FIG. 6 shows how the cell cover 21 is arranged in order to press the wafer 19 tightly, whereby a preset pressing power is ensured by the stepped edge design between the cell cover 21 and the middle part (=cell frame or frame part formed by the upper half cell 5 and the lower half cell 3). The cell cover 21 can be fastened using screws, which are screwed into threaded holes 45 in the upper half cell 5.

The cell cover of the device according to the invention can contain a plug that can move normally with respect to the back side of the wafer 19 and that is adapted by gas pressure to the back side of the wafer 19. Thus, the front side of the wafer presses on the ring seal, and the test chamber is therefore sealed. This has the advantage that wafers 19 of various thicknesses can be inserted, e.g., bonded and thus thicker wafers 19, and this also has the advantage that the pressing force can be varied (ring seals of various hardnesses).

A corresponding arrangement is provided on the underside of the device 1 according to the invention, so that here, too, the anode plate 25 is pressed tightly against the ring seal 23 with a preset path and thus a preset pressing power by the stepped edge design between the middle part (cell frame or frame part) and the underlying anode cover 27 in FIG. 6.

In the case of the device according to the invention, the sealing of the wafer is carried out either, as is usual, on the edge of the wafer or else also directly on the microchips or in general within the wafer surface.

With a seal directly on the microchips or away from the edge of the wafer 19, it is possible to measure wafers with varying diameters but a constant size of the ring seal (O-ring) with constant cell geometry.

Thus, the measuring signals, which are obtained from different wafer sizes, can be compared directly to one another. This produces a greater flexibility, since different wafer sizes can be measured, which in addition produces a lower expense in the case of managing measuring data, which is transparent and thus reliable.

Preferably, the wafer 19 is contacted with two or more than two contact pins 17, which are arranged distributed uniformly on the film 15 over the periphery of the wafer.

The sealing forces (the extent of the pressing, the O-rings provided as ring seals 13 and 23) are defined by impact of the cell cover 21 and the anode cover 27 on the cell frame, which is formed by the half cells 3 and 5.

It is preferred when the device 1 according to the invention is obliquely oriented horizontally by an acute angle, e.g., 45°, and the wafer 19 is arranged in such a way that its wafer front side points downward and comes into contact with the electrolyte, which flows through the test chamber 7.

Since a vertical orientation of the device 1 is not possible (falling out of the ring seal 13) and a horizontal orientation of the device 1 can be disadvantageous, since gas bubbles, which have an electrically insulating effect, can collect and accumulate, the above-mentioned oblique orientation of the device 1 according to the invention is advantageous.

For each measurement of the properties, a (new) test wafer is required. The test wafer is produced in a normal production process with usual wafers, added to the device 1 according to the invention as a measuring apparatus, whereby test wafers can be reused multiple times (can be recycled), so that for this purpose, there are no high costs.

Thanks to the arrangement of the device 1 according to the invention at an acute angle to the horizontal and at an advantageous working height, as well as the position of the wafer 19 within the device 1 and the described design of the ring seal 13, a wafer 19 can be inserted quickly and securely (manually or automatically) into the device 1 and can be removed from the latter.

In the case of the device 1 according to the invention, it is provided that the electrolyte enters through the opening 41 into the test chamber 7 of the device 1, flows in a laminar flow through the test chamber 7, and leaves the latter again through the opening 43 and enters the plant infrastructure.

The plant infrastructure contains at least one tank for the electrolyte, but preferably multiple electrolyte tanks, and a pump (e.g., a centrifugal pump) for uniform circulation of the electrolyte, a tank for ultrapure water or at least a connection for ultrapure water for flushing the device 1 with water, a connection for inert gas for drying the device 1, and in addition the necessary valves, lines, regulators and measuring instruments.

The at least one guide 37 that is provided in the test chamber 7 of the device 1 supports the device 1 in the area of the test chamber 7 and is advantageous for a laminar design of the flow through the test chamber 7.

The at least one guide 37 can also be the point at which a chemically inert reference electrode 31 is inserted in wire or sheet form into the test chamber 7. As an alternative, the reference electrode 31 can also be designed by a reference electrode of the second type according to the state of the art.

When a centrifugal pump is used for circulating the electrolyte, the flow rate of the electrolyte in the device 1 can be easily adjusted by changing the rotational speed of the impeller.

The anode plate 25 is, as can be seen from the drawings, contacted on its back side. The anode plate 25, which is used in the device 1 according to the invention, is coated in an electrically conductive and chemically inert manner on both sides. For example, platinum is used as a coating material.

With the method according to the invention, immediate measurements, i.e., immediately after a production run, can be made of, e.g., a metal layer on a wafer 19. This makes it possible, directly in the device 1 according to the invention, to perform direct measurements (i.e., checking the original process result, e.g., the original nickel layer).

This namely direct method according to the invention is advantageous compared to indirect methods, such as, e.g., the characterization of the electrolyte using other equipment and with derivation of electrolyte quality from layer quality.

The device 1 according to the invention is designed in such a way that it can be easily incorporated into a plant infrastructure and that modifications of the device 1 can be easily performed.

A possible additional function of the device 1 according to the invention is as follows:

Instead of a chemically inert anode plate 25, a plate that consists of a thermoplastic, such as, e.g., polypropylene, with two chemically inert wires or rods that are welded-in or cast-in at right angles to the plate and that are adjacent to one another, but electrically insulated from one another, can also be used. In this case, the anode plate 25 is used instead of the wafer 19. One of the two wires or rods then functions as a cathode and one as a reference electrode. This configuration of three chemically inert electrodes can be used for characterizing electrolytes.

In summary, an embodiment of the invention can be described as follows:

To test wafers, microchips, etc., electrical properties thereof are periodically measured and stored electrochemically. The measured values are compared to one another in order to determine changes in the electrical properties. For executing the method, a device 1 that is designed as a measuring cell is provided, which device has a test chamber 7 between an upper half cell 5 and a lower half cell 3, through which chamber the electrolyte is directed. The test chamber 7 is closed by a cell cover 21, which at the same time presses a wafer 19 against a ring seal 13 toward the upper half cell 5. The opening that forms the test chamber 7 in the lower half cell 3 is closed by a ring seal 23, an anode plate 25, and an anode cover 27.

The invention claimed is:

1. Method for testing electrically conducting objects, comprising steps of:
   periodically detecting electrical properties of the objects electrochemically,
   storing characteristics of the thus detected electrical properties,
   applying statistical methods in order to compare the thus detected characteristics of electrical properties of various objects to one another,
   determining a tendency of changes in characteristics of the electrical properties, and
   evaluating the tendency to detect changes in electrical properties of objects;
   wherein a comparison of characteristics of electrical properties of an object with the mean values of the characteristics of electrical properties of objects produced in advance is made,
   wherein as electrical properties, current-voltage curves, current-time curves, voltage-time curves, impedance, resistance and capacity are all detected, and
   wherein for the current-voltage curves, current-time curves, voltage-time curves, as characteristics of the curves, an increase in the current in the case of a defined voltage and in the voltage in the case of a defined time, various objects can be compared to one another.

2. Method according to claim 1, wherein electrical properties of objects are detected periodically and at specified intervals.

3. Method according to claim 1, wherein a comparison of characteristics of electrical properties of objects produced in succession is made.

4. Method according to claim 1, wherein a comparison of characteristics of electrical properties of objects produced in succession is made using statistical methods.

5. Method according to claim 1, wherein the properties of electrically conductive layers, surfaces and/or interfaces of objects are detected.

6. Device for testing electrically conducting objects for executing the method according to claim 1, the device comprising:
   A measuring cell with a test chamber (7) through which the electrolyte flows,
   A holding device for the object to be tested in the cell,
   An inlet opening (41) and an outlet opening (43) for the electrolyte into and from the test chamber (7) of the device (1),
   At least one anode (35),
   At least one contact pin (17) that is to be placed on the object (19) that is to be tested in order to contact the latter, and
   At least one reference electrode (31);
   wherein the test chamber (7) is inclined horizontally at an acute angle.

7. Device according to claim 6, wherein the anode is designed as an anode plate (25).

8. Device according to claim 7, wherein instead of the anode plate (25), a plate with at least two chemically inert electrodes, which are poled as a cathode and a reference electrode, is used.

9. Device according to claim 6, wherein the measuring cell comprises two cover parts (21, 27) and a middle part that is arranged between the latter, and wherein the test chamber (7) is provided in the middle part.

10. Device according to claim 9, wherein the middle part is formed by an upper half cell (5) and a lower half cell (3).

11. Device according to claim 10, wherein a seal (13) is provided on the side of the middle part that is near to the object to be tested.

12. Device according to claim 11, wherein the seal (13) rests on the object (19) to be tested.

13. Device according to claim 10, wherein the test chamber (7) is formed by recesses in the half cells (3 and 5) and is closed by the cover parts (21 and 27).

14. Device according to claim 9, wherein a cover part is a cell cover (21) and the other cover part is an anode cover (27).

15. Device according to claim 9, wherein the anode plate (25) is arranged between an anode cover (27) and the middle part, in the lower half cell (3) thereof.

16. Device according to claim 9, wherein the the inlet opening and the outlet opening (41 and 43) are provided in the lower half cell (3).

17. The device for testing electrically conducting objects of claim 6, wherein the acute angle is 45°.

18. Method for testing electrically conducting objects, comprising steps of:
   periodically detecting electrical properties of the objects electrochemically,
   storing characteristics of the thus detected electrical properties,
   applying statistical methods in order to compare the thus detected characteristics of electrical properties of various objects to one another,
   determining a tendency of changes in characteristics of the electrical properties, and
   evaluating the tendency to detect changes in electrical properties of objects;
   wherein characteristics of current-voltage-time curves or current-time curves are detected at selected points thereof,
   wherein as characteristics of the curves, an increase in the current in the case of a defined voltage and in the voltage in the case of a defined time, various objects are compared to one another, and
   wherein the points are characteristic of the quality of the surface of the object.

19. The device for testing electrically conducting objects of claim 18, wherein the surface is a cathode surface.

20. The device for testing electrically conducting objects of claim 19, wherein the cathode surface is a wafer surface.

21. The device for testing electrically conducting objects of claim 18, wherein the surface is a cathode layer.

22. The device for testing electrically conducting objects of claim 18, wherein the surface is a cathode interface.

* * * * *